US012653391B2

(12) United States Patent (10) Patent No.: US 12,653,391 B2
Ding et al. (45) Date of Patent: Jun. 16, 2026

(54) METHODS AND SYSTEMS FOR REALTIME MONITORING AND CLEANING OF A LAPAROSCOPIC LENS

(71) Applicant: Covidien LP, Mansfield, MA (US)

(72) Inventors: Weijiang Ding, Shanghai (CN); Syed Sarfraz Ahamed, Shanghai (CN); Kai Huang, Shanghai (CN); Kaizhi Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 540 days.

(21) Appl. No.: 17/910,996

(22) PCT Filed: Mar. 12, 2020

(86) PCT No.: PCT/CN2020/078996
§ 371 (c)(1),
(2) Date: Sep. 12, 2022

(87) PCT Pub. No.: WO2021/179249
PCT Pub. Date: Sep. 16, 2021

(65) Prior Publication Data
US 2023/0165452 A1 Jun. 1, 2023

(51) Int. Cl.
*A61B 1/12* (2006.01)
*A61B 1/00* (2006.01)
(Continued)

(52) U.S. Cl.
CPC .......... *A61B 1/126* (2013.01); *A61B 1/00009* (2013.01); *A61B 1/00154* (2013.01); *A61B 1/015* (2013.01); *A61B 1/3132* (2013.01)

(58) Field of Classification Search
CPC ............ A61B 1/00135; A61B 1/00142; A61B 1/00154; A61B 1/015; A61B 1/126;
(Continued)

(56) References Cited

U.S. PATENT DOCUMENTS 5,575,756 A * 11/1996 Karasawa ............ A61B 1/0014
600/156
9,039,604 B2 * 5/2015 Yoshida ............. A61B 17/3474
604/266
(Continued)

FOREIGN PATENT DOCUMENTS

CN 203458369 U 3/2014
CN 103997622 A 8/2014
(Continued)

OTHER PUBLICATIONS

European Search Report dated Nov. 2, 2023, issued in corresponding EP Appln. No. 20924699, 7 pages.
(Continued)

*Primary Examiner* — Ryan N Henderson
(74) *Attorney, Agent, or Firm* — Dymera IP, LLC

(57) ABSTRACT

A system for monitoring and cleaning a lens of a laparoscope interoperative includes a monitoring system having a laparoscope and software for monitoring clarity of an image provided by the laparoscope. The software being configured to provide a feedback signal when the image clarity falls below a predetermined threshold. The system further includes a cleaning system in operative connection with the monitoring system and configured to activate upon receipt of the feedback signal from the monitoring system. The cleaning system includes a source of pressurized liquid, a source of compressed air, and a source of suction. The sources of pressurized liquid and compressed air are configured to be activated simultaneously with the source of suction.

20 Claims, 9 Drawing Sheets

(51) Int. Cl.
 *A61B 1/015* (2006.01)
 *A61B 1/313* (2006.01)
(58) Field of Classification Search
 CPC ..... A61B 1/127; A61B 1/00009; A61B 1/313;
 A61B 1/3132; A61B 1/12
 See application file for complete search history.

(56) References Cited

U.S. PATENT DOCUMENTS

| | | | | |
|---|---|---|---|---|
| 9,078,694 | B2 * | 7/2015 | Hartoumbekis | A61B 1/126 |
| 11,583,176 | B2 * | 2/2023 | Aluru | A61B 1/126 |
| 11,751,759 | B2 * | 9/2023 | Burt | A61B 17/34 |
| | | | | 600/117 |
| 11,805,968 | B2 * | 11/2023 | Aluru | A61B 1/126 |
| 12,150,625 | B2 * | 11/2024 | Aluru | A61B 1/126 |
| 2006/0069306 | A1 | 3/2006 | Banik et al. | |
| 2007/0255106 | A1 | 11/2007 | Kawanishi | |
| 2007/0282253 | A1 * | 12/2007 | Sasaki | A61B 1/313 |
| | | | | 604/93.01 |
| 2008/0045859 | A1 * | 2/2008 | Fritsch | A61B 18/148 |
| | | | | 600/567 |
| 2008/0081948 | A1 * | 4/2008 | Weisenburgh | A61B 1/126 |
| | | | | 600/157 |
| 2008/0255424 | A1 * | 10/2008 | Durgin | A61B 10/0283 |
| | | | | 600/156 |
| 2009/0234193 | A1 * | 9/2009 | Weisenburgh | A61B 1/00068 |
| | | | | 600/157 |
| 2009/0299137 | A1 * | 12/2009 | Gal | A61B 1/128 |
| | | | | 600/116 |
| 2010/0010310 | A1 * | 1/2010 | Weisenburgh, II | A61B 1/3132 |
| | | | | 600/156 |
| 2011/0237880 | A1 | 9/2011 | Hamel et al. | |
| 2013/0041230 | A1 * | 2/2013 | Hartoumbekis | A61B 17/3421 |
| | | | | 600/205 |
| 2013/0053643 | A1 * | 2/2013 | Yoshida | A61B 1/126 |
| | | | | 600/114 |
| 2013/0331730 | A1 * | 12/2013 | Fenech | A61B 1/00009 |
| | | | | 600/560 |
| 2015/0190041 | A1 * | 7/2015 | Suehara | A61B 1/127 |
| | | | | 600/109 |
| 2017/0035277 | A1 * | 2/2017 | Kucharski | A61B 1/05 |
| 2017/0238795 | A1 * | 8/2017 | Blumenkranz | B08B 3/02 |
| 2018/0014908 | A1 * | 1/2018 | Katz | A61B 1/00135 |
| 2018/0344427 | A1 * | 12/2018 | Rosenbaum | A61B 90/70 |
| 2019/0053861 | A1 * | 2/2019 | Lwin | A61B 1/005 |
| 2019/0125176 | A1 * | 5/2019 | Burt | G02B 23/2476 |
| 2021/0127963 | A1 * | 5/2021 | Aluru | A61B 1/126 |
| 2021/0127964 | A1 * | 5/2021 | Aluru | A61B 1/126 |
| 2021/0236749 | A1 * | 8/2021 | Kokhanenko | A61B 17/3421 |
| 2021/0322684 | A1 * | 10/2021 | Fischer | A61M 13/003 |
| 2022/0175237 | A1 * | 6/2022 | De Abreu | A61B 1/00135 |
| 2022/0192480 | A1 * | 6/2022 | Burt | A61B 1/00006 |
| 2023/0165452 | A1 * | 6/2023 | Ding | A61B 1/00135 |
| | | | | 600/114 |
| 2023/0414085 | A1 * | 12/2023 | Aluru | A61B 1/126 |
| 2024/0293018 | A1 * | 9/2024 | Aluru | A61B 1/126 |

FOREIGN PATENT DOCUMENTS

| | | |
|---|---|---|
| CN | 107072521 A | 8/2017 |
| CN | 107647905 A | 2/2018 |
| CN | 109222879 A | 1/2019 |
| CN | 109823312 A | 5/2019 |
| DE | 202007004031 U1 | 6/2007 |

OTHER PUBLICATIONS

International Search Report and Written Opinion dated Dec. 10, 2020, issued in corresponding international application No. PCT/CN2020/078996, 6 pages.
Chinese Official Action dated Sep. 30, 2024, issued in corresponding Chinese Appln. No. 202080098377.9, 7pgs.
Chinese Office Action, Chinese Application No. 202080098377.9, Apr. 19, 2025, 5pgs.
Chinese Application No. 202080098377.9, Rejection Decision dated Jun. 30, 2025, 10pgs.

* cited by examiner

212

400

212b

214

METHODS AND SYSTEMS FOR REALTIME MONITORING AND CLEANING OF A LAPAROSCOPIC LENS

CROSS-REFERENCE TO RELATED APPLICATION

This application is a national stage entry of PCT/CN2020/078996 under 35 U.S.C. § 371(a) filed on Mar. 12, 2020, the disclosure of which is incorporated herein by reference in its entirety.

FIELD

The disclosure relates to a surgical apparatus for use in minimally invasive surgical procedures, such as endoscopic and/or laparoscopic procedures and, more particularly, to systems and methods for monitoring and cleaning the lens of an endoscope or laparoscope.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula assemblies are extended into and left in place in the abdominal wall to provide access for endoscopic surgical tools. A camera or scope is inserted through a cannula assembly to permit the visual inspection and magnification of the body cavity. The surgeon can then perform diagnostic and/or therapeutic procedures at the surgical site with the aid of specialized instrumentation, such as forceps, graspers, cutters, applicators, and the like, which are designed to fit through additional cannulas.

In use, a lens of a scope can become covered by condensation, tissue, blood, other body fluids, etc. Keeping the lens of a laparoscope clean during a procedure is thus difficult, and the time needed to clean the scope during the procedure can increase both the overall time of the procedure and the amount of time a patient needs to remain under anesthesia, both of which can lead to increased risk of infection and increased recovery time.

SUMMARY

A system for monitoring and cleaning a lens of a laparoscope interoperative includes a monitoring system having a laparoscope and a software for monitoring clarity of an image provided by the laparoscope. The software being configured to provide a feedback signal when the image clarity falls below a predetermined threshold. The system further includes a cleaning system in operative connection with the monitoring system and configured to activate upon receipt of the feedback signal from the monitoring system. The cleaning system includes a source of pressurized liquid, a source of compressed air, and a source of suction. The sources of pressurized liquid and compressed air are configured to be activated simultaneously with the source of suction.

In certain aspects of the disclosure, the system includes an access assembly in operable engagement with the monitoring system and the cleaning system. The access assembly may include a cannula assembly configured to receive the laparoscope. The system may include a positioning mechanism for positioning the laparoscope relative to the cannula assembly. The cannula assembly may include a distal portion and a vacuum seal disposed on the distal portion of the cannula assembly.

In some aspects of the disclosure, the source of pressurized liquid is be configured to provide a water jet. The temperature of the water in the water jet may be 37° C. The salinity of the water in the water jet may be 9,000 ppm. The source of compressed air may be configured to provide $CO_2$. The positioning mechanism may be configured to move the laparoscope relative to the cannula assembly to a position where a vacuum seal on a distal portion of the cannula assembly is distal to the lens of the laparoscope. Alternatively, or in addition, the positioning mechanism may be configured to move the cannula assembly relative to the laparoscope to a position where a vacuum seal on a distal portion of the cannula assembly is distal to the lens of the laparoscope.

A method of monitoring and cleaning a lens of a laparoscope includes monitoring clarity of an image provided by a laparoscope, identifying when the image clarity falls below a predetermined threshold, and signaling to a cleaning system that the image clarity fell below the predetermined threshold. The method further includes activating a source of pressurized liquid, activating a source of suction, and activating a source of compressed air.

In certain aspects of the disclosure, the method further includes positioning a lens of the laparoscope distal of a vacuum seal of a cannula assembly of an access assembly through which the laparoscope is received. The activating of the source of pressurized liquid may be performed simultaneously with the activating of the source of suction. The activating of the source of compressed air may be performed simultaneously with the activating of the source of suction. The positioning of the lens of the laparoscope may be performed automatically. The identifying when the image clarity falls below a predetermined threshold may include comparing a real time single frame image with a sharpness comparison template.

BRIEF DESCRIPTION OF THE DRAWINGS

Various aspects of the disclosed systems and methods are described herein below with reference to the drawings, wherein.

DETAILED DESCRIPTION

Figure 1:
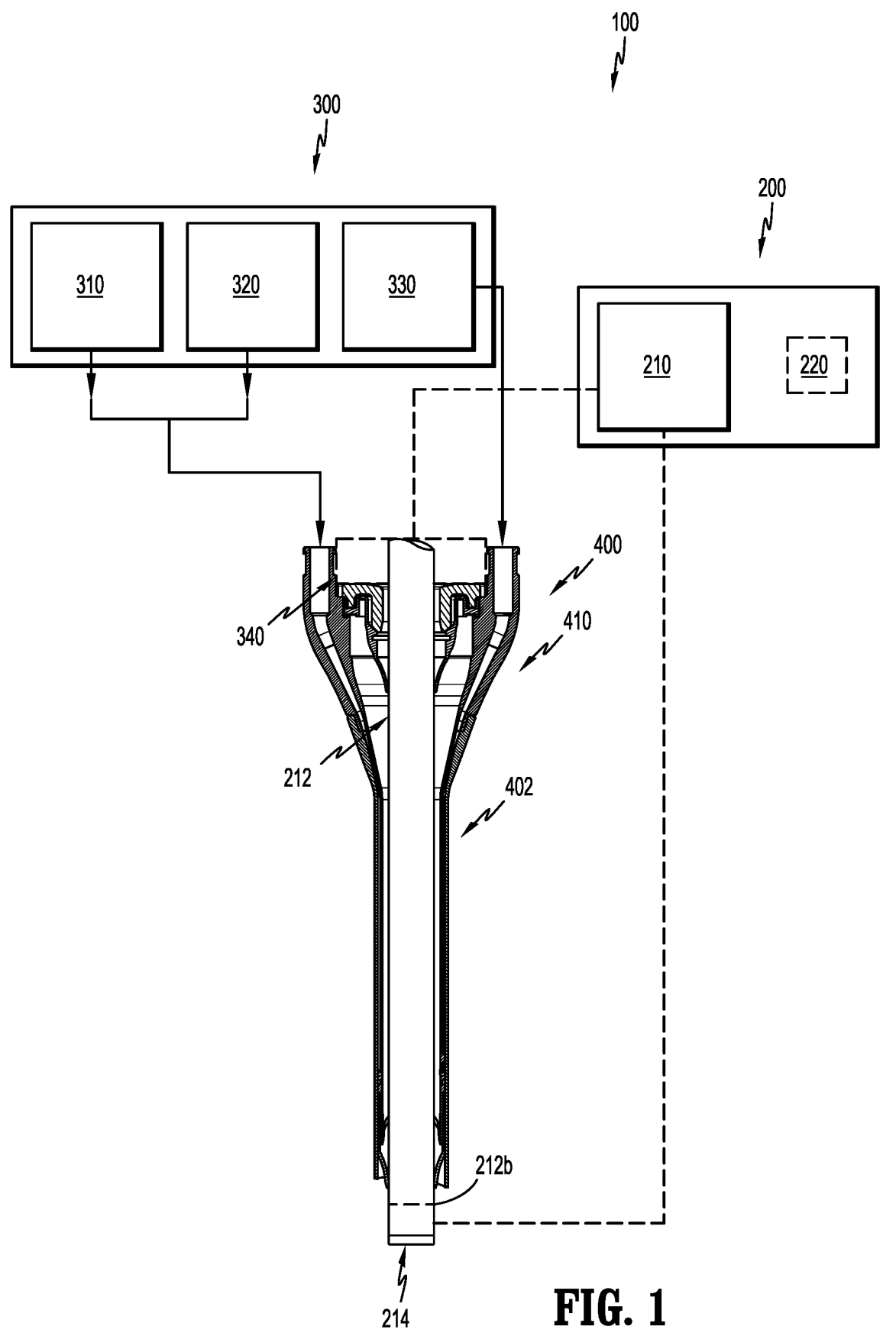
FIG. 1 is a diagram of a system for monitoring and cleaning a lens of a laparoscope according to aspects of the disclosure.

The lens monitoring and cleaning systems and methods are described in detail with reference to the drawings, in which like reference numerals designate identical or corresponding elements in each of the several views. As used herein the term "distal" refers to that portion of the trocar, or component thereof, farther from the user, while the term "proximal" refers to that portion of the trocar, or component thereof, closer to the user. In addition, the term "laparoscopic" or "laparoscope" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel. As used herein, the term "about" means that the numerical value is approximate and small variations would not significantly affect the practice of the disclosed aspects of the disclosure. Where a numerical limitation is used, unless indicated otherwise by the context, "about" means the numerical value can vary by +10% and remain within the scope of the disclosure.

Disclosed are systems and methods of smart real-time self-cleaning laparoscopy lens interoperative, e.g., during a surgical procedure. As will be described in further detail below, the systems and methods utilize real time monitoring and analysis of image quality to maintain image clarity. The system monitors the image clarity through the lens of the laparoscope and if the image clarity is lower than a predetermined threshold, the system will send a feedback signal to cleaning system which will initiate a cleaning process. The systems and methods maintain a clean lens, e.g., image clarity, in real time and automatically interoperative, thereby reducing surgery time, and reducing risk.

FIG. 1 illustrates a flow diagram of a monitoring and cleaning system according to aspects of the disclosure shown generally as monitoring and cleaning system 100. The monitoring and cleaning system 100 includes a monitoring system 200 for monitoring image clarity and identifying when the image clarity falls below a predetermined threshold, a cleaning system 300 initiated upon receipt of a feedback signal provided by the monitoring system 200, and an access assembly 400 through which a laparoscope 212 of the monitoring system 200 is received and is configured for operation with the monitoring system 200 and the cleaning system 300.

The monitoring system 200 may include a laparoscopic imaging system 210 having a laparoscope 212. The laparoscopic imaging system 210 may be programmed to monitor image clarity through a lens 214 of the laparoscope 212 and provide a feedback signal to the cleaning system 300 when the image clarity falls below a predetermined threshold. Alternatively, the monitoring system 200 may include an independent processor 220 for monitoring image clarity and initiating lens cleaning.

The software program for monitoring the image clarity includes an algorithm for determining whether the image clarity is less than a predetermined threshold. In particular, the algorithm compares a real time single frame image with a sharpness comparison template. If the image clarity is less than the predetermined threshold, the software communicates with the cleaning system 300, e.g., outputs a sign to the cleaning system 300. In one aspect of the disclosure, if the program shows as a "yes" sign, the cleaning system 300 automatically starts and runs a lens cleaning program.

The laparoscopic imaging system 210 and/or the independent processor 220, may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

The cleaning system 300 includes a positioning assembly 310 for positioning the distal end 212*b* of the laparoscope 212 within the cannula assembly 410 of the access assembly 400. In this manner, the lens 214 of the laparoscope 212 is enclosed within the cannula assembly 410 to permit cleaning of the lens 214. The positioning assembly 310 may include a mechanism for advancing the cannula assembly 410 about the distal end 212*b* of the laparoscope 212 to enclose the distal end 212*b* of the cannula assembly 410 within the cannula assembly 410. In addition, or alternatively, the positioning assembly 310 may include a mechanism for retracting the laparoscope 212 relative to the cannula assembly 410 to position the distal end 212*b* of the laparoscope 212 within the cannula assembly 410.

The cleaning system 300 includes a source of pressurized liquid 310, e.g., saline, for cleaning the lens 214 and a source of compressed air 320, e.g., CO2, for drying the lens 214. In certain aspects of the disclosure, the source of pressurized liquid 330 is a water jet and the temperature of the water is 37° C., and a salinity of the water from about 8,000 ppm to about 10,000 ppm or from about 0.8% to about 1.0%. Similarly, the $CO_2$ or other gas of the source of compressed air 340 may also have a temperature of 37° C. to prevent fogging.

To maintain equilibrium within the cannula assembly 410 during the cleaning and drying process, the cleaning system 300 includes a source of negative pressure or suction 330, e.g., vacuum. As will be described in further detail below, the source of suction 330 is activated during activation of the pressurized liquid and/or compressed air to equalize the pressure within the access assembly 400 and remove the water and $CO_2$ used to clean and dry the lens 214.

Optionally, the cleaning system 300 includes a positioning assembly 340 for positioning the distal end 212*b* of the laparoscope 212 within the cannula assembly 410 of the access assembly 400. In this manner, the lens 214 of the laparoscope 212 is enclosed within the cannula assembly 410 to permit cleaning of the lens 214. The positioning assembly 310 may include a mechanism for advancing the cannula assembly 410 about the distal end 212*b* of the laparoscope 212 to enclose the distal end 212*b* of the laparoscope 212 within the cannula assembly 410. In addition, or alternatively, the positioning assembly 340 may include a mechanism for retracting the laparoscope 212 relative to the cannula assembly 410 to position the distal end 212*b* of the laparoscope 212 within the cannula assembly 410.

Figure 2:
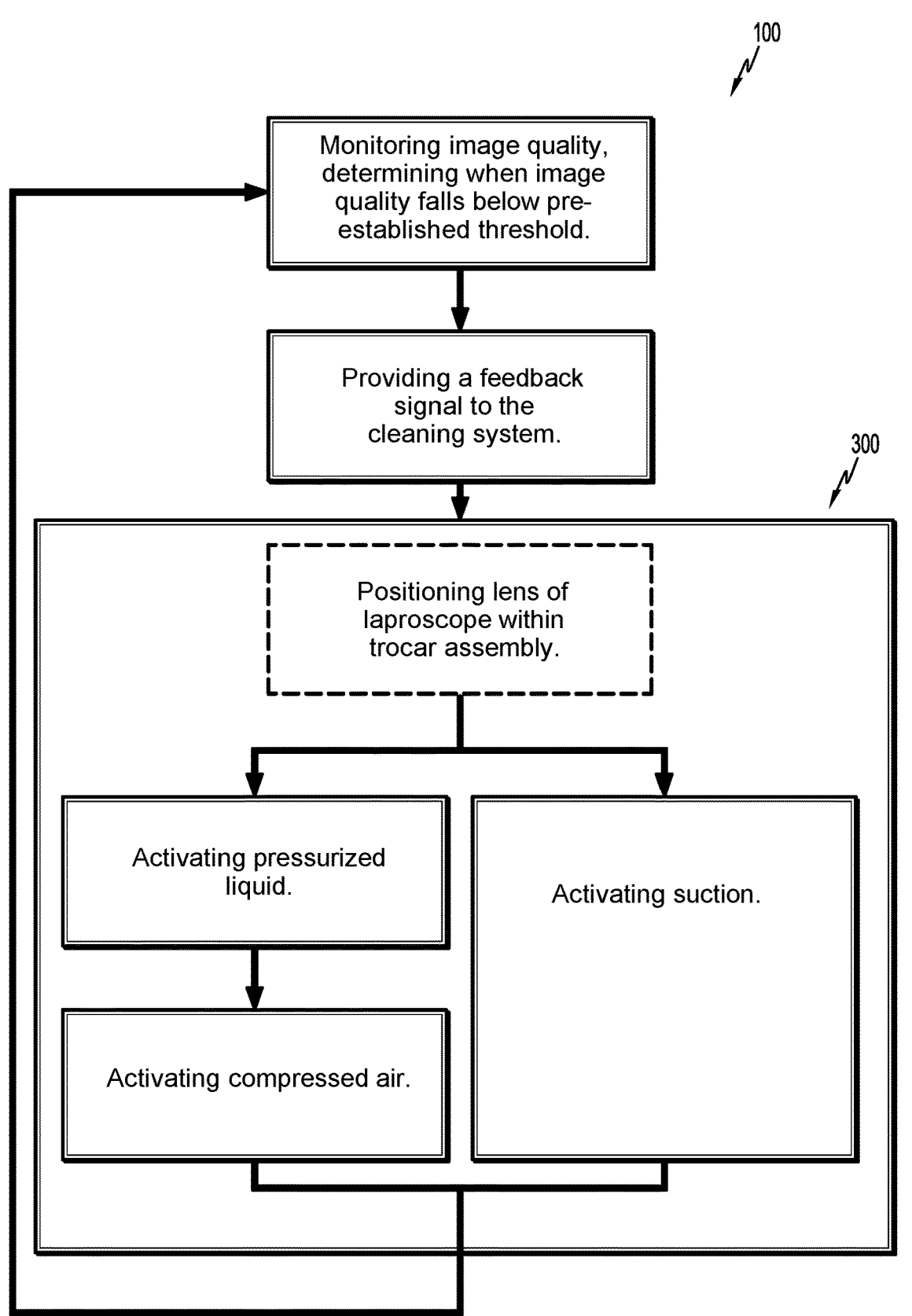
FIG. 2 is a flow chart of a method of monitoring and cleaning a lens of a laparoscope according to aspects of the disclosure.
Figure 3:
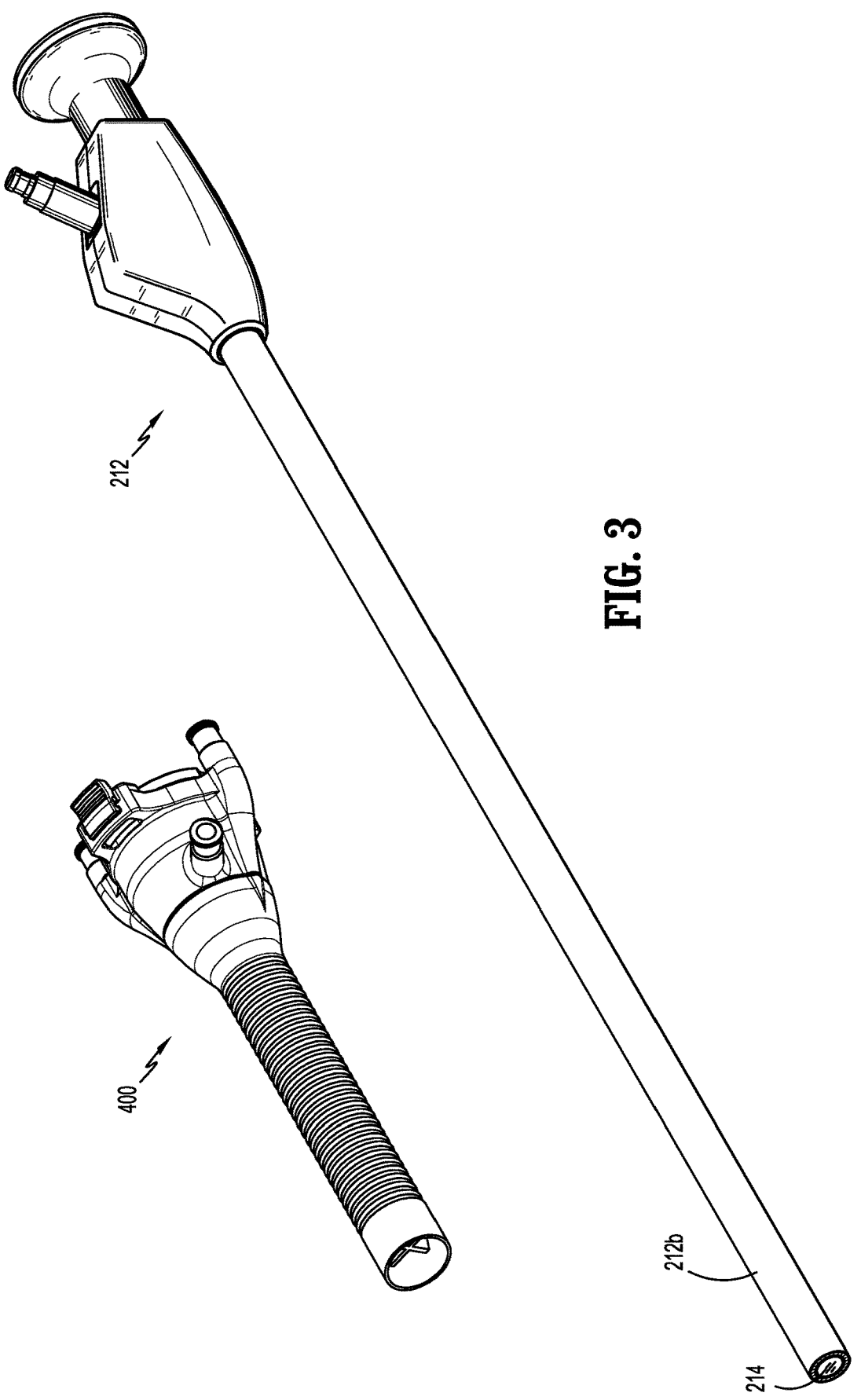
FIG. 3 is a side perspective view of an access assembly and laparoscope of the disclosure.

FIG. 2 illustrates a flow diagram of the method according an aspect of the disclosure. As noted above, the monitoring system 200 may be a laparoscopic imaging system 210 including software for monitoring image clarity of the image provided through the lens 214 (FIG. 1) of the laparoscope 212, and identifying when the image clarity falls below a predetermined threshold. Alternatively, the software for monitoring image clarity may be an independent processor in operable connection with the laparoscopic imaging system 210. The software for monitoring image clarity is further configured to provide a feedback signal to the cleaning system 300 (FIG. 1) when the image clarity falls below the predetermined threshold.

Once the monitoring system 200 determines that the image clarity fell below the predetermined threshold, and the feedback signal alerts the cleaning system 300 that the image clarity has fallen below the predetermined threshold, the cleaning system 300 is initiated to clean the lens 214 of the laparoscope.

Prior to the washing of the lens 214 of the laparoscope 212, if the distal end 212*b* of the laparoscope 212 is not already positioned with the access assembly 400, e.g., with the distal end 212*b* of the laparoscope 212 proximal of a vacuum seal 450 (FIG. 5) on a distal portion 416 of a cannula assembly 410 of the access assembly 400, at least one of, the laparoscope 212 is retracted and the cannula assembly 410 is advanced. It is envisioned that either or both of these actions may be performed manually or automatically. When the retraction/advancement is automatic, as noted above, the cleaning system 300 may include the positioning assembly 340 for positioning the distal end 212*b* of the laparoscope 212 relative to the vacuum seal 450 of the cannula assembly 410.

After confirming that the distal end 212*b* of the laparoscope 212 of the monitoring system 200 is disposed within the cannula assembly 410 distal of the tip protector 430, the source of pressurized liquid 310 is activated to spray the distal end 212*b* of the laparoscope 212, including the lens 214, with a water jet to clean the lens 214. As noted above, in certain aspects of the disclosure, the water jet includes water having a temperature of 37° C. and a salinity of between about 8,000 ppm and about 10,000 ppm, or between about 0.8% and about 1.0%, and in certain aspects, about 9,000 ppm or 0.9% salinity. The length of time of that the source of pressurized liquid is activated may be based on clarity of the image prior to initiation of the cleaning system 300. Less clarity of the image produced by the conventional laparoscopic imaging system 210 may result in a longer period of activation of the source of pressurized liquid 300, while the period of activation of the source of pressurized liquid 300 for an image clarity at or slightly above the threshold value may be shorter.

Simultaneously with the activation of the source of pressurized liquid 310 is activation of the source of suction 330. By activating the source of pressurized fluid 310 simultaneously with the activation of the source of suction 330, equilibrium is maintained within the cannula assembly 410, and the integrity of closed space provided by the tip protector 450 is maintained.

After the source of pressurized liquid 310 has been activated for the predetermined amount of time, based on the image clarity or other factors, the source of pressurized liquid 310 is deactivated and the source of compressed air 320 is activated. In certain aspects of the disclosure, the compressed $CO_2$ has a temperature of 37° C. to match the temperature of the water from the source of pressurized liquid 310 to prevent fogging of the lens 214 of the laparoscope 212. The source of suction 330 remains active during the activation of the source of pressurized liquid 310 to maintain the equilibrium within the cannula assembly 410.

After a predetermined period of time, and thorough drying of the lens 214 of the laparoscope 212, both the source of compressed air 320 and the source of suction 330 are deactivated. Following the cleaning of the lens 214 of the laparoscope 212, the laparoscope 212 is ready for continued use.

It is envisioned that the entire cleaning process, from determination that the image clarity fell below the predetermined threshold, to the completion of the drying of the lens 214 of the laparoscope, is ten seconds (10*s*). It is envisioned that the cleaning process may take more or less than ten seconds (10*s*). It is also envisioned that the system and methods disclosed herein may be expanded to robotic surgery systems to maintain image quality.

It is envisioned that the systems and the methods of the disclosure enhance surgical efficiency, maintain image quality, reduce cleaning lens time and times, reduce surgical operation and anesthesia time, reduces the risk of infection as lens of the laparoscope is cleaned away from the surgical site.

FIGS. 3-6 illustrate the access assembly 400 in accordance with an aspect of the disclosure and a laparoscope 212 of a monitoring system 210 (FIG. 1). Although the system and method of the disclosure are shown with reference to access assembly 400, it is envisioned that the aspects of the disclosure may be modified for use with access assemblies having alternative configurations.

Figure 4:
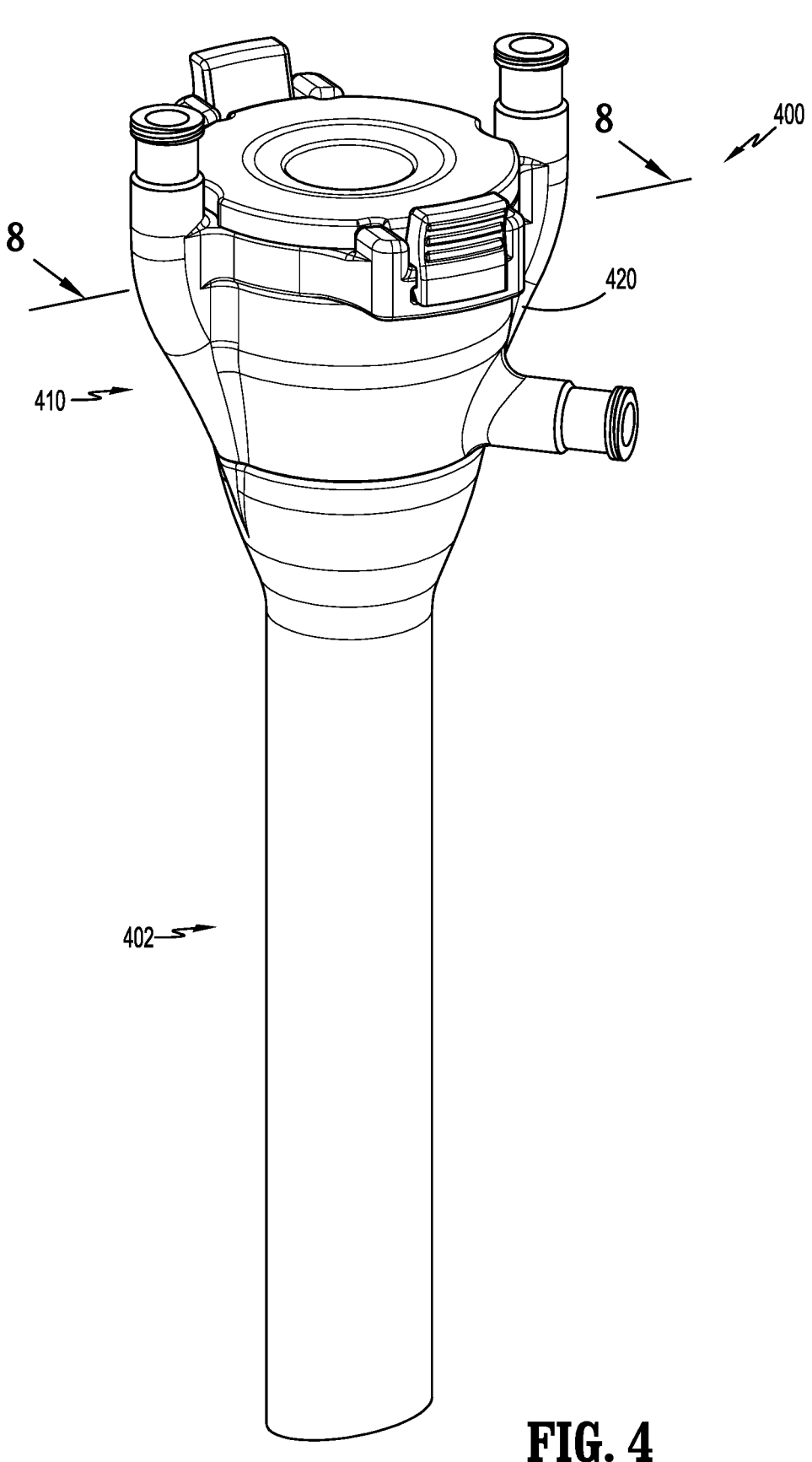
FIG. 4 is a side view of a cannula assembly of FIG. 3.
Figure 5:
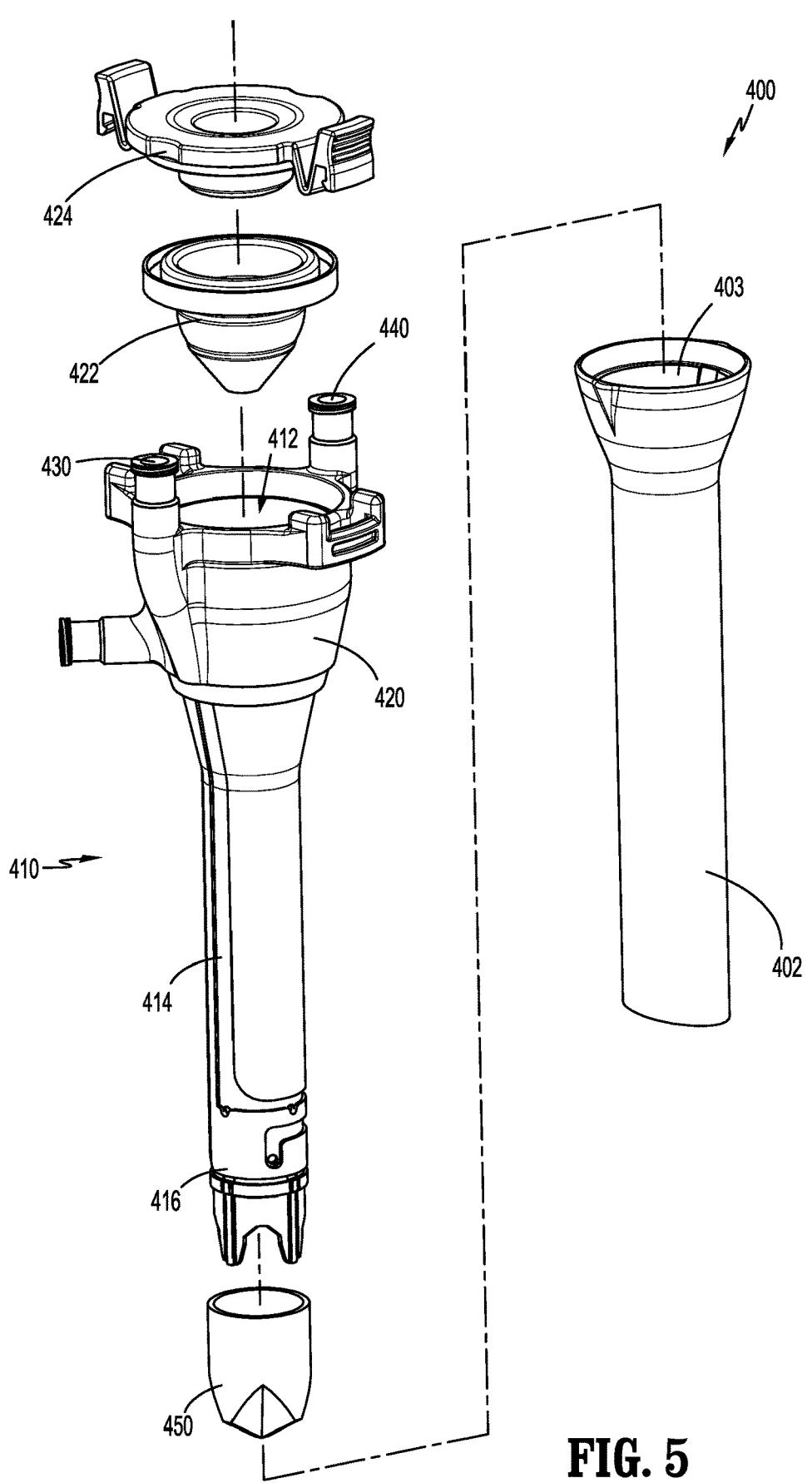
FIG. 5 is an exploded perspective view, with parts separated, of the cannula assembly of the disclosure.

As shown in FIG. 5, the access assembly 400 includes a cannula 402 defining a lumen 403, and a cannula assembly 410 receivable through the lumen 403 of the cannula 402. The cannula assembly 410 has a lumen 412 through which a medical device may pass, e.g., laparoscope 212. The cannula assembly 410 includes a seal assembly 420, an elongate body 414, a distal portion 416, and a proximal portion 418. As shown in FIG. 4, the seal assembly 420 includes a seal 422 for placement therein and a securing collar 424 for maintaining the seal 422 within the seal assembly 420. The cannula assembly 410 also has an inlet port 430 configured for operable engagement with the source of pressurized liquid 310 (FIG. 1) and the source of compressed air 320, and a vacuum port 440 configured for operable connection with the source of suction 330.

Figures 6, 7:
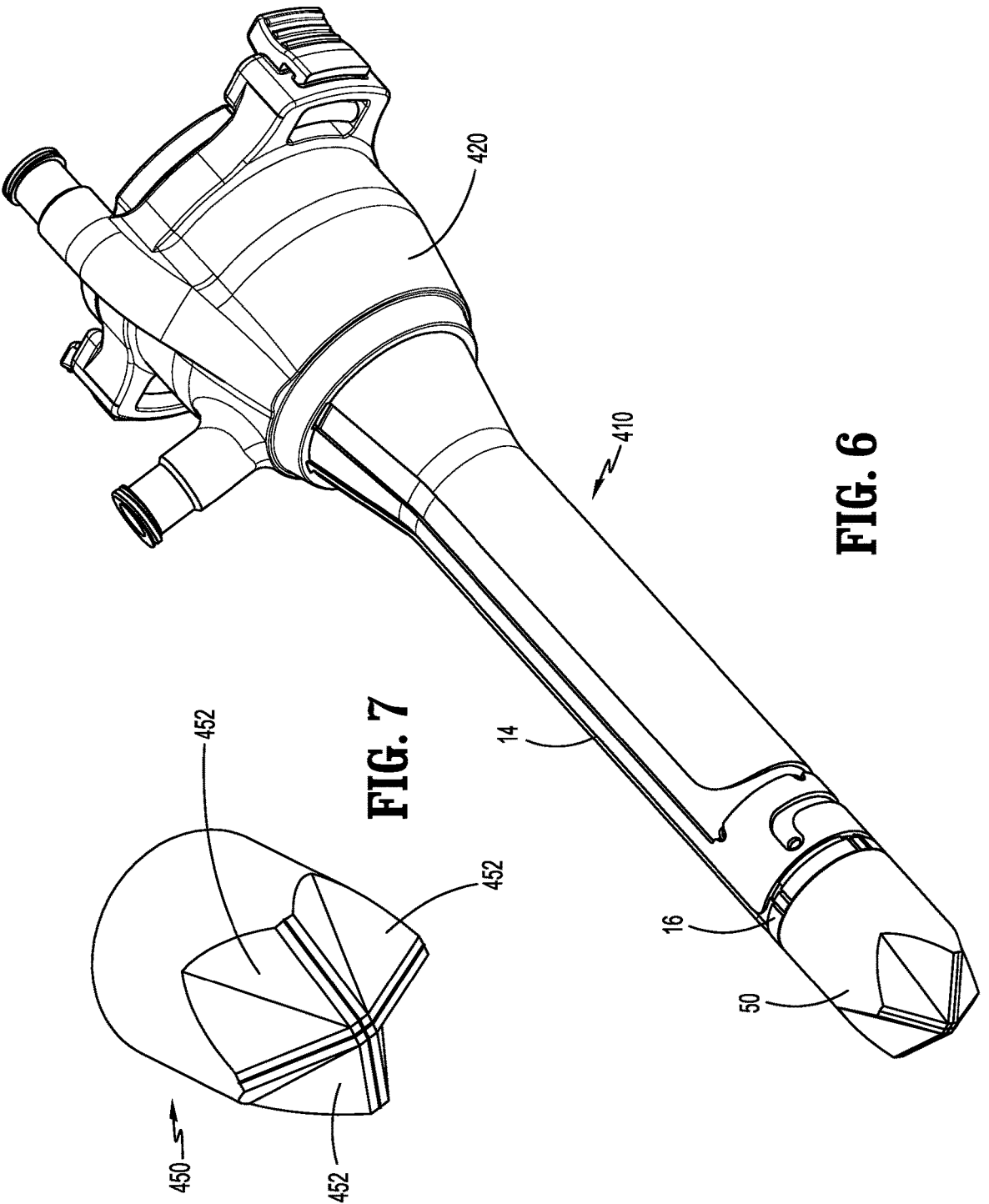
FIG. 6 is a side partial cut-away view of the cannula assembly of FIG. 3.
FIG. 7 is a side perspective view of a seal of the cannula assembly shown in FIG. 5 located at a distal portion of the cannula assembly of the disclosure.

The cannula assembly 410 also has a vacuum seal 450 at the distal portion 416 of the cannula assembly 410 (FIGS. 5-7). As shown in greater detail in FIG. 7, the vacuum seal 450 may be formed of multiple leaflets 452 which permit passage of a medical device therethrough, but the multiple leaflets 452 will close the vacuum seal 450 when a medical device is removed therefrom. Moreover, a vacuum drawn on the vacuum port 440, will maintain the vacuum seal 450 in a closed position.

Figure 8:
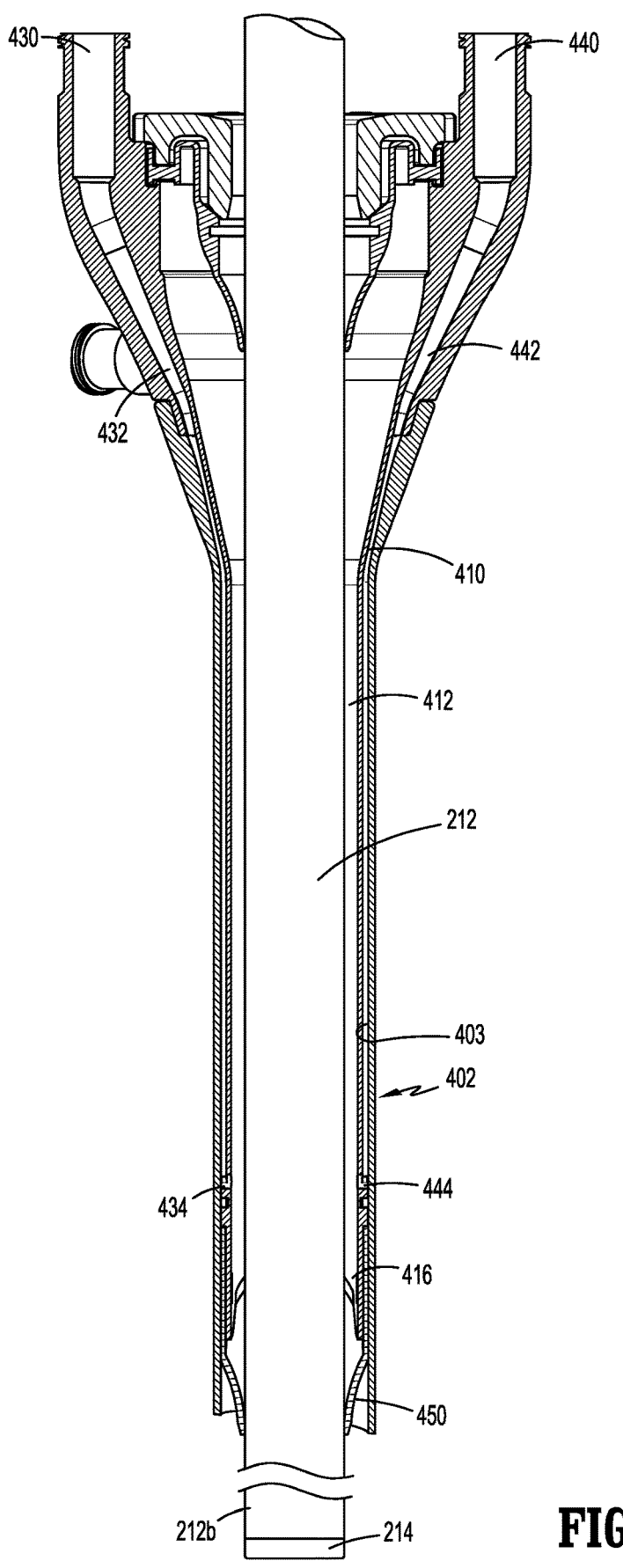
FIG. 8 is a cross-sectional side view of the cannula assembly of FIG. 4, taken along section line 8-8 of FIG. 4 with a laparoscope inserted therethrough.

FIG. 8 shows a laparoscope 212 deployed from the cannula assembly 410 through the cannula 402. The vacuum seal 450 is opens when the laparoscope 212 passes therethrough. As shown in FIG. 8, the inlet port 430 is connected to inlet tube 432, which terminates at entry opening 434 at the distal portion 416 of the cannula assembly 410. The inlet port 430, inlet tube 432 and entry opening 434 permit the introduction of liquids and/or gases into the distal portion 416 of the cannula assembly 410. Similarly, the vacuum port 440 is connected to outlet tube 442, which terminates at exit opening 444 at the distal portion 416 of the cannula assembly 410. The vacuum port 440, outlet tube 442 and exit opening 444 permit the removal of liquids and/or gases from the distal portion 416 of the cannula assembly 410.

Figure 9:
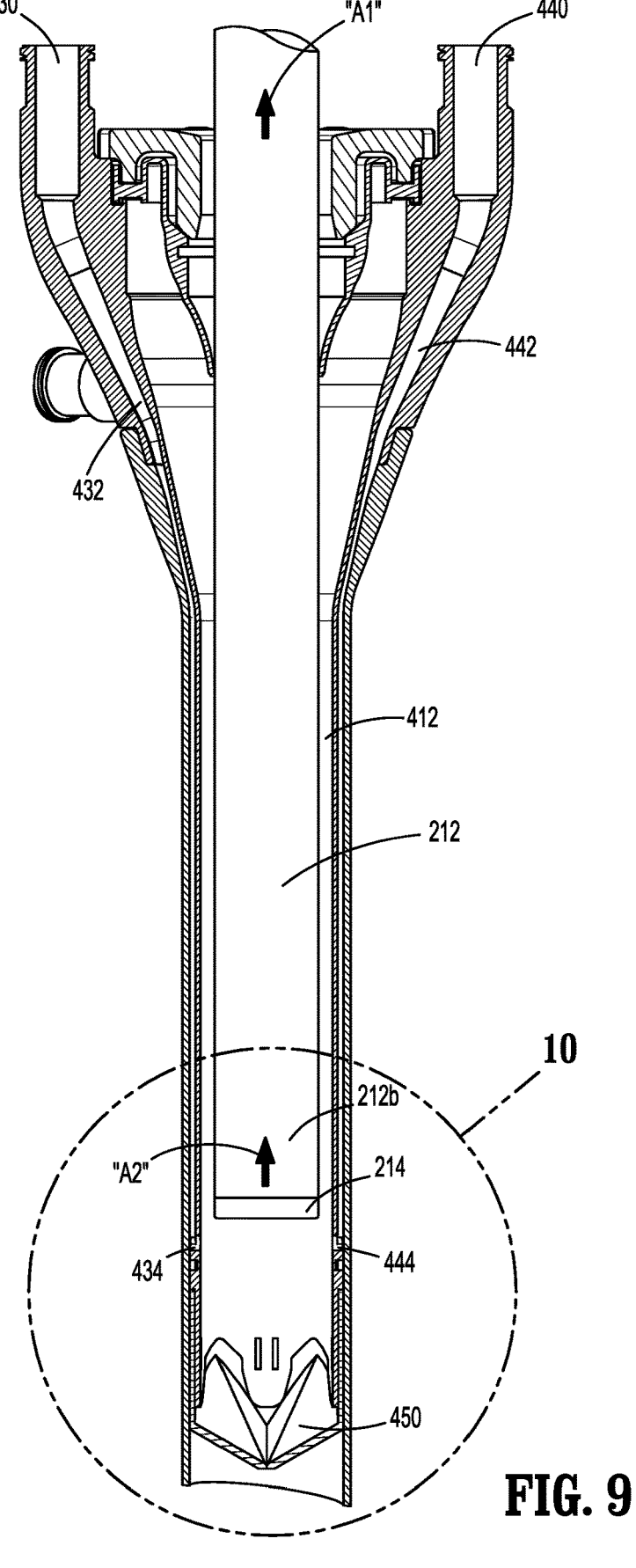
FIG. 9 is a side cross-sectional view of the cannula assembly of FIG. 8 showing withdrawal of a laparoscope.
Figure 10:
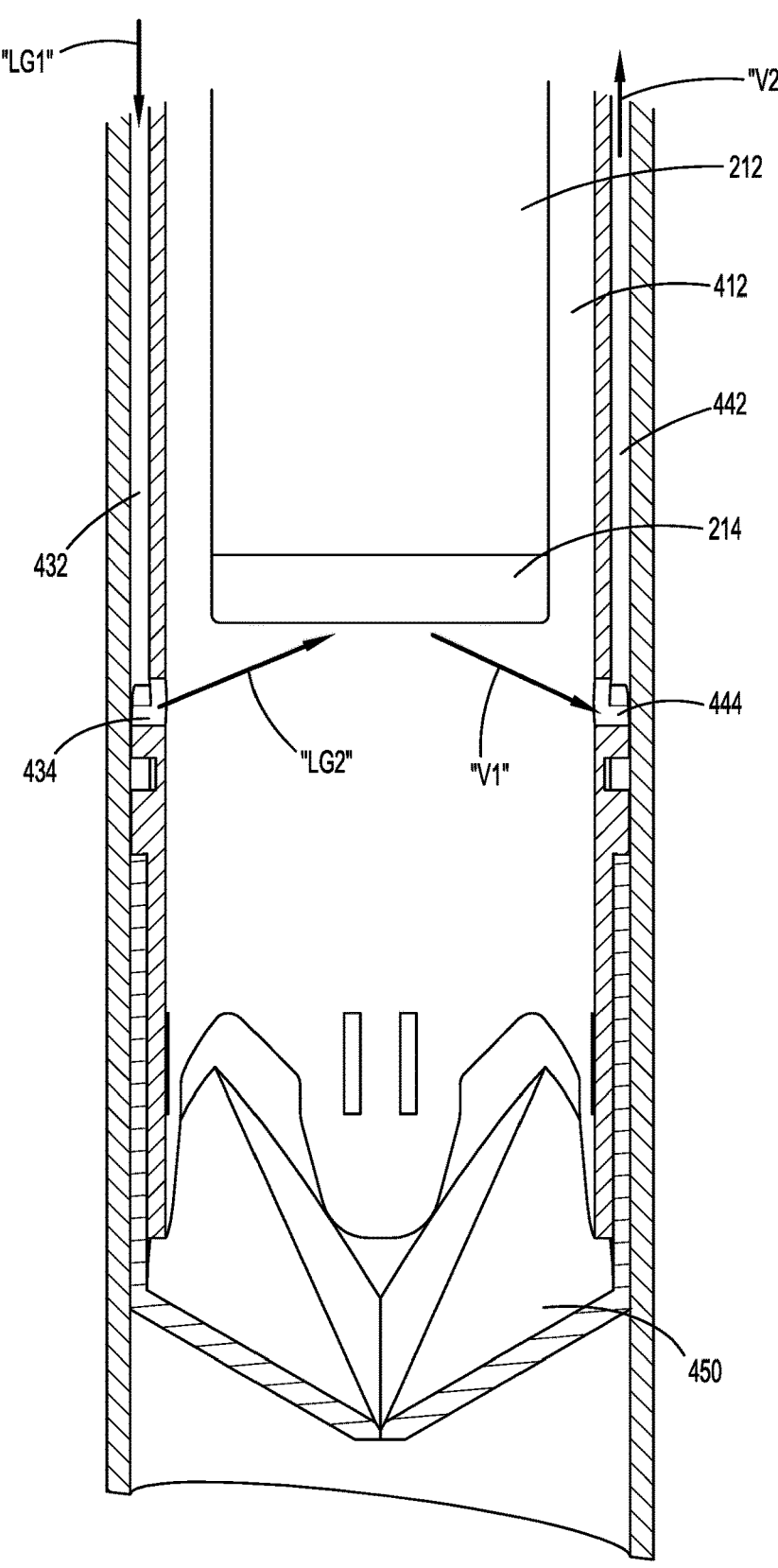
FIG. 10 is an enlarged view of the indicated area of detail shown in FIG. 9.

In use, as shown in greater detail in FIGS. 9 and 10, the laparoscope 212 in need of cleaning is partially withdrawn proximally within the cannula assembly 410 (indicated by arrows "A1" and "A2" in FIG. 9) so that the lens 214 of the laparoscope 212 is proximal to the vacuum seal 450. A vacuum is drawn by connecting the source of suction 330 (FIG. 1) to the vacuum port 440. Drawing of the vacuum causes the vacuum seal 450 to form a tight seal.

Liquids and/or gases are then introduced through the inlet port 430. Drawing the vacuum causes the liquids and/or gases to travel through the inlet tube 432, shown as arrow "LG1", and pass through the entry opening 434 into the distal portion 416 of the cannula assembly 410, shown as arrow "LG2", where liquids and/or gases contact the lens 214 of the laparoscope 212, to remove any condensation, tissue, blood, other body fluids, etc. from the lens 214.

Continued drawing of the vacuum causes the liquids, gases, and any other material(s) removed from the laparoscope lens 214 to exit the distal portion 416 of the cannula assembly 410, shown as arrow "V1", by passing through exit opening 444 and through the outlet tube 442, shown as arrow "V2", and out of the cannula assembly 410 through the vacuum port 440.

Any of the components described herein may be fabricated from either metals, plastics, resins, composites or the like taking into consideration strength, durability, wearability, weight, resistance to corrosion, ease of manufacturing, cost of manufacturing, and the like. In aspects, the elongate body of the cannula assembly may be made of metals, such as stainless steel, while the seals may be formed of an elastomeric plastic or rubber.

It will be understood that various modifications may be made to the disclosed methods and systems. Therefore, the above description should not be construed as limiting, but merely as exemplifications of aspects of the disclosure. Those skilled in the art will envision other modifications within the scope and spirit of the disclosure. For example, any and all features of one described aspect may be suitably incorporated into another aspect.

What is claimed is:

1. A system for interoperative monitoring and cleaning a lens of a laparoscope, the system comprising:
   a monitoring system including a laparoscope and software for monitoring clarity of an image provided by the laparoscope, the software being configured to determine whether the image clarity is below a predetermined threshold, and provide a feedback signal upon determining that the image clarity is below the predetermined threshold; and
   a cleaning system in operative connection with the monitoring system and being configured to activate upon receipt of the feedback signal from the monitoring system, the cleaning system, being in operative connection to an access assembly, comprising:
      a cannula having an outer surface and an inner surface, the inner surface defining a first lumen; and
      a trocar configured for reception into the first lumen of the cannula, the trocar having an outer surface and an inner surface, the outer surface having at least a first channel and a second channel, the inner surface defining a second lumen configured to receive the laparoscope, the trocar comprising an inlet tube being formed by the first channel and the inner surface of the cannula and an outlet tube being formed by the second channel and the inner surface of the cannula; and
   wherein the cleaning system is configured, in response to receipt of the feedback signal, to activate a source of pressurized liquid and a source of compressed air through the inlet tube, and a source of suction through the outlet tube, and wherein the source of pressurized liquid and the source of compressed air are configured to be activated simultaneously with the source of suction.

2. The system of claim 1, wherein the access assembly is in operable engagement with the monitoring system.

3. The system of claim 1, wherein the laparoscope is retractable or advanceable for positioning the laparoscope relative to the trocar.

4. The system of claim 1, wherein the trocar includes a distal portion and a vacuum seal disposed on the distal portion of the trocar.

5. The system of claim 1, wherein the source of pressurized liquid is configured to provide a water jet.

6. The system of claim 5, wherein the temperature of the water in the water jet is 37° C.

7. The system of claim 5, wherein the salinity of the water in the water jet is 9,000 ppm.

8. The system of claim 1, wherein the source of compressed air is configured to provide $CO_2$.

9. The system of claim 1, wherein the laparoscope is movable relative to the trocar to a position in which the lens of the laparoscope is proximal to a vacuum seal on a distal portion of the trocar.

10. The system of claim 1, wherein the trocar is movable relative to the laparoscope to a position in which the lens of the laparoscope is proximal to a vacuum seal on a distal portion of the trocar.

11. A system for interoperative monitoring and cleaning a lens of a laparoscope, the system comprising:
   a monitoring system including a laparoscope and software for monitoring clarity of an image provided by the laparoscope, the software being configured to determine whether the image clarity is below a predetermined threshold, and provide a feedback signal upon determining that the image clarity is below the predetermined threshold; and
   a cleaning system in operative connection with the monitoring system and being configured to activate upon receipt of the feedback signal from the monitoring system, the cleaning system being in operative connection to an access assembly, comprising:
      a cannula having an outer surface and an inner surface, the inner surface defining a first lumen; and
      a trocar configured for reception through the first lumen of the cannula, the trocar having an outer surface and an inner surface, the outer surface having at least a first channel and a second channel, the inner surface defining a second lumen configured to receive the laparoscope, the trocar comprising:
         an inlet tube being formed by the first channel and the inner surface of the cannula, the inlet tube having a first portion extending substantially longitudinally with respect to the trocar, and a second portion extending substantially circumferentially with respect to the trocar; and
         an outlet tube being formed by the second channel and the inner surface of the cannula; and wherein the cleaning system is configured, in response to receipt of the feedback signal, to activate a source of pressurized liquid and a source of compressed air through the inlet tube simultaneously with a source of suction through the outlet tube.

12. The system of claim 11, wherein the cleaning system is configured to activate automatically in response to the feedback signal from the monitoring system.

13. The system of claim 11, wherein the source of pressurized liquid is configured to provide a jet of water.

14. The system of claim 13, wherein the temperature of the water is 37° C.

15. The system of claim 13, wherein the salinity of the water is 9,000 ppm.

16. The system of claim 11, wherein the source of compressed air is configured to provide $CO_2$.

17. The system of claim 11, wherein the laparoscope is movable relative to the trocar to a position in which the lens of the laparoscope is proximal to a vacuum seal at a distal portion of the trocar.

18. The system of claim 11, wherein the trocar is movable relative to the laparoscope to a position where a vacuum seal at a distal portion of the trocar is distal to the lens of the laparoscope.

19. The system of claim 1, wherein the inlet tube includes a first portion extending substantially longitudinally with respect to the trocar, and a second portion extending substantially circumferentially with respect to the trocar.

20. The system of claim 19, wherein the second portion of the inlet tube tapers to terminate at an entry opening into the second lumen.

\* \* \* \* \*